United States Patent [19]
Strome et al.

[11] Patent Number: 6,015,419
[45] Date of Patent: Jan. 18, 2000

[54] RETRACTABLE SURGICAL SCALPEL

[75] Inventors: Scott E. Strome, Rochester; Edward T. Joseph, Inver Grove Heights, both of Minn.

[73] Assignee: Strome Steel Surgical, Inc., Ann Arbor, Mich.

[21] Appl. No.: 09/143,833

[22] Filed: Aug. 31, 1998

[51] Int. Cl.$^7$ .................................................. A61B 17/32
[52] U.S. Cl. .............................. 606/167; 606/170; 30/62
[58] Field of Search ................................ 606/167, 170, 606/172; 30/62, 335, 526

[56] References Cited

U.S. PATENT DOCUMENTS

| | | | |
|---|---|---|---|
| 4,958,625 | 9/1990 | Bates et al. | 606/167 |
| 5,330,493 | 7/1994 | Haining | 606/167 |
| 5,342,379 | 8/1994 | Volinsky | 606/167 |
| 5,344,424 | 9/1994 | Roberts et al. | 606/167 |
| 5,431,672 | 7/1995 | Cote et al. | 606/167 |
| 5,571,127 | 11/1996 | DeCampli | 606/167 |
| 5,662,669 | 9/1997 | Abindin et al. | 606/167 |
| 5,830,231 | 11/1998 | Geiges, Jr. | 606/167 |

*Primary Examiner*—Michael Buiz
*Assistant Examiner*—Jonathan D. Goldberg
*Attorney, Agent, or Firm*—Welsh & Katz, Ltd.

[57] ABSTRACT

A surgical instrument includes a hollow handle having an end slot and a side slot and a blade carrier securable to a scalpel blade and moveable between first and second positions relative to the handle. One of the first and second positions is an extended, in-use position wherein the scalpel blade extends out of the handle through the end slot. The other position is a retracted, non-use position wherein the scalpel blade is wholly disposed within the handle. At least one finger extends from the blade carrier and has a first contoured portion engageable, when the blade carrier is in the first position, with a second contoured portion of the handle. The first and second contoured portions are substantially complementary such that the finger must deflect to permit disengagement of the first contoured portion of the finger from the second contoured portion of the handle so that the blade carrier can be moved from the first position toward the second position. A locking cam is moveable between a locked position wherein the locking cam substantially inhibits deflection of the finger of the blade carrier and an unlocked position wherein the locking cam permits deflection of the finger of the blade carrier. A method of using this surgical instrument includes the steps of moving the locking cam to the unlocked position if the locking cam is in the locked position, moving the blade carrier from the first position to the second position or from the second position to the first position, and moving the locking cam to the locked position.

20 Claims, 1 Drawing Sheet

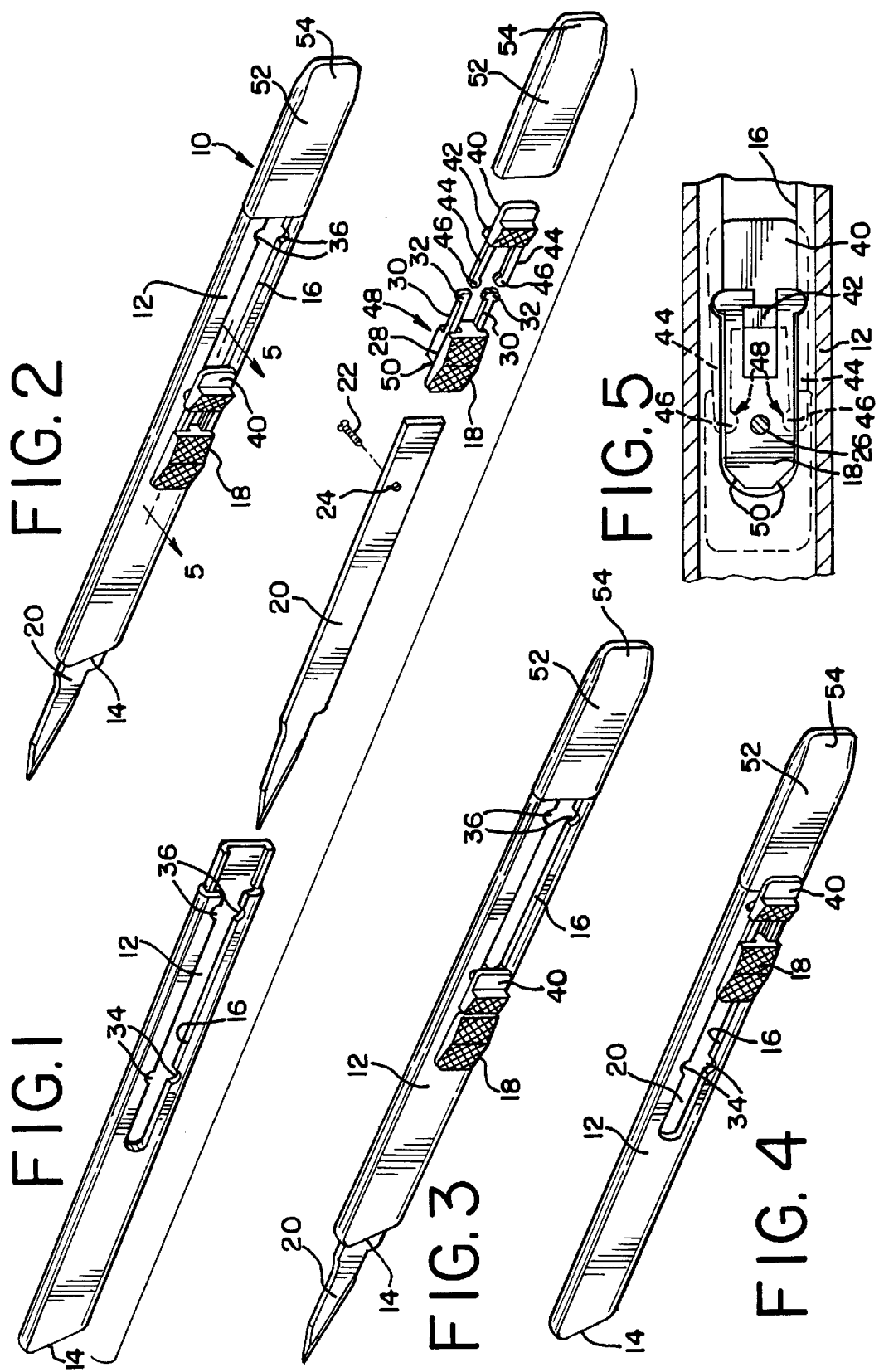

RETRACTABLE SURGICAL SCALPEL

TECHNICAL FIELD

The present invention relates generally to hand-held instruments used, for example, in hospitals for surgery as well as in other medical contexts. More particularly, the present invention relates to a preferably disposable surgical instrument such as a scalpel having a blade that may be retracted into a handle portion of the instrument when the blade is not in use.

BACKGROUND

Surgical scalpels typically include a replaceable, surgical steel scalpel blade that is secured, either permanently or removably, at one end of a metal handle. While these prior-art scalpels work well to perform various surgical procedures, users of such scalpels often sustain accidental injuries which is obviously highly undesirable. For example, scrub nurses may be injured when loading and unloading replaceable scalpel blades. Similarly, surgeons and surgical assistants may be injured as the scalpel is transferred back and forth among the members of a surgical team or during surgical dissection when the blunt end of the surgical instrument (opposite the blade) is used as a special-purpose instrument, such as for defining surgical planes, which is a common practice among surgeons.

To alleviate the problem of injuries caused by conventional, prior-art scalpels, several attempts have been made to develop a scalpel in which the blade of the scalpel can be retracted into the handle of the scalpel. Examples of these attempts are disclosed in Haining U.S. Pat. No. 5,330,493, issued Jul. 19, 1994 ("the '493 Patent"), Roberts, et al. U.S. Pat. No. 5,344,424, issued Sep. 6, 1994 ("the '424 Patent"), Cote, et al. U.S. Pat. No. 5,431,672, issued Jul. 11, 1995 ("the '672 Patent"), and DeCampli U.S. Pat. No. 5,571,127, issued Nov. 5, 1996 ("the '127 Patent"). Each of these patents discloses a scalpel having a blade which may be retracted or extended by the actuation of a single pushbutton followed by a manual sliding of that pushbutton to effect either retraction of the blade of the scalpel into the handle of the scalpel or extension of the blade from the handle.

Although these scalpels may reduce, to a limited extent, the injuries described above, they also have a number of drawbacks of their own. It is important in the performance of surgical procedures that the blade of a scalpel be fixed relative to the handle, because any movement of the blade relative to the handle that is not intended or expected by a surgeon can result in serious injury to a patient in surgery. Some patient injuries also can occur because, in the case of some prior-art scalpels, the blade does not extend far enough out of the handle to enable a surgeon to effectively use the entire cutting edge of the blade for cutting rather than merely the point. The use of the point of a scalpel blade for cutting increases the risk of a surgeon "sticking" the patient with the scalpel blade, which also is highly undesirable.

Moreover, the scalpels disclosed in the foregoing patents suffer from the additional drawback that the blade of each of those scalpels can make slight lateral movements relative to handle (i.e., transverse to a longitudinal axis of the handle), even when the blade is locked in an exposed position. Further, because of the single-action (i.e., one-button) structure used for extension and retraction of the blade of the each of those scalpels, it is common for a surgeon to actuate the button inadvertently while maneuvering the scalpel and thereby unintentionally cause the scalpel blade to retract partially or fully into the handle of the scalpel, which is highly undesirable, especially during emergency surgical procedures and the like.

SUMMARY OF THE INVENTION

Clearly, there is a need for a surgical instrument that is safer to handle and use than the above-described fixed-blade and retractable-blade scalpels. The present invention substantially reduces the risk of many of the injuries inflicted by prior-art scalpels by providing a surgical instrument with a scalpel blade that can be retracted into a handle portion of the instrument, such as when the instrument is transferred between members of a surgical team or when the blunt end of the instrument handle (opposite the blade) is being used. Further, when the blade is extended, it is securely fixed relative to the handle such that it does not move laterally relative to the handle when in use. The blade also cannot easily be inadvertently retracted when it is locked in an extended position. The instrument of the present invention, if disposable, also eliminates the need for a scrub nurse to manually replace scalpel blades and thereby also obviates the inherent risk of injury associated with that procedure. In short, safety is a primary advantage of the present invention.

A retractable surgical scalpel according to the present invention is therefore designed to significantly reduce the risk of accidental injuries and cross-contamination resulting from unintended contact with the scalpel blade. The invention achieves this by providing a dual locking mechanism that allows the blade of the scalpel to be positively locked in an extended position when the blade is in use and to be retracted completely within the handle portion of the instrument when the blade is not in use, permitting both safe use of the instrument and safe disposal of the instrument after use.

According to one aspect of the present invention, a surgical instrument includes a hollow handle having an end slot and a side slot, retraction means for securably moving a scalpel blade between first and second positions relative to the handle, and locking means for locking the retraction means in one of the first and second positions. The retraction means comprises a first sliding element securable to a scalpel blade and having at least one finger extending therefrom. The finger has a first contoured portion that is engageable, when the retraction means is in the first position, with a second contoured portion of the handle. The first and second contoured portions are substantially complementary such that the finger must deflect to permit disengagement of the first contoured portion of the finger from the second contoured portion of the handle so that the retraction means can be moved from the first position toward the second position. The locking means comprises a sliding element moveable between a locked position and an unlocked position. The second sliding element has a cam that permits deflection of the finger of the first sliding element when the second sliding element is in the unlocked position and substantially inhibits deflection of the finger of the first sliding element when the second sliding element is in the locked position.

Preferably, the first contoured portion of the finger comprises a tab on the finger substantially projecting toward an adjacent edge of the side slot, and the second contoured portion of the handle comprises a notch formed in the adjacent edge of the side slot. Alternatively, the first contoured portion of the finger can comprise a notch in the edge of the finger adjacent an edge of the side slot, and the second contoured portion can then comprise a tab on the adjacent edge of the side slot substantially projecting toward the finger.

In one embodiment, the sliding element has a pair of fingers, each having a contoured portion that, when the retraction means is in the first position, is engageable with a respective contoured portion of the handle. The contoured portion of each finger is substantially complementary to the respective contoured portion of the handle such that each finger must deflect to permit disengagement of the contoured portion of that finger from a respective contoured portion of the handle so that the retraction means can be moved from the first position toward the second position. In this embodiment, the cam preferably permits deflection of both fingers when the second sliding element is in the unlocked position and substantially inhibits deflection of both fingers when the second sliding element is in the locked position.

The handle of the instrument of the present invention may be provided with a third contoured portion with which the first contoured portion of the finger is engageable when the retraction means is in the second position. The third contoured portion is substantially complementary with the first contoured portion such that the finger must deflect, once again, to permit disengagement of the first contoured portion from the third contoured portion so that the retraction means can be moved from the second position toward the first position.

Means may be provided for biasing the finger toward an adjacent edge of the side slot. In one embodiment, the finger is flexible but substantially resilient such that the first contoured portion generally may remain in contact with the adjacent edge of the side slot. Alternatively, a spring, for example, can be provided for biasing the finger(s) toward an adjacent edge of the side slot.

The invention thus contemplates a surgical instrument having a hollow handle with an end slot and a slide slot, a retraction means for securably moving a scalpel blade between first and second positions relative to the handle, one of which is an extended, inuse position wherein the scalpel blade extends out of the handle through the end slot, and the other of which is a retracted, non-use position wherein the scalpel blade is wholly disposed within the handle, and a locking means for locking the retraction means in one of the first and second positions relative to the handle. The retraction means includes a first sliding element securable to a scalpel blade and having at least one finger extending therefrom. The finger has a first contoured portion engageable, when the retraction means is in the first position, with a second contoured portion of the handle, and the first and second contoured portions are substantially complementary such that the finger must deflect to permit disengagement of the first contoured portion of the finger from the second contoured portion of the handle so that the retraction means can be moved from the first position toward the second position. The locking means includes a second sliding element moveable between a locked position and an unlocked position and having a cam that permits deflection of the finger of the first sliding element when the second sliding element is in the unlocked position and substantially inhibits deflection of the finger of the first sliding element when the second sliding element is in the locked position.

In accordance with the present invention, a method of locking a scalpel blade of such a surgical instrument comprises the steps of moving the retraction means to one of the first and second positions relative to the handle and locking the retraction means in one of the first and second positions with the locking means.

A method of using a retractable surgical scalpel according to the present invention includes the steps of moving a locking cam to the unlocked position thereof if the locking cam is in the locked position, moving a blade carrier from one of first and second positions thereof to the other of the first and second positions, and moving the locking cam to the locked position.

BRIEF DESCRIPTION OF THE DRAWINGS

FIG. 1 is an exploded view of a surgical instrument according to the present invention;

FIG. 2 is a perspective of an assembled surgical instrument with a scalpel blade locked in an extended or "in-use" position;

FIG. 3 is a perspective similar to FIG. 2, wherein the scalpel blade is in the extended, "in-use" position thereof, but unlocked;

FIG. 4 is a perspective similar to FIGS. 2 and 3, wherein the scalpel blade is locked in a retracted or "non-use" position; and FIG. 5 is a fragmentary, sectional view of the surgical instrument of FIG. 2 taken along the lines 5—5 therein.

DESCRIPTION OF THE PREFERRED EMBODIMENTS

The preferred embodiment of the retractable scalpel generally comprises a handle and a scalpel blade. The handle is hollow and substantially flat having a width greater than its thickness and a substantially longer length. Projections, grips, bumps, or other friction-enhancing means may be provided on the handle to inhibit the instrument from slipping out of a user's hand. One end of the handle is blunt or slightly rounded while the other end of the handle contains a slot. A mechanism for moving the scalpel blade between an extended, in-use position and a retracted, non-use position is also provided with the handle. In the extended position, the cutting portion of the blade extends through the slot in the end of the handle and is disposed outside of the handle. In the retracted position, the blade is fully retracted within the handle where the blade cannot be accidentally contacted by an individual handling the instrument. The end slot mentioned above is substantially rectangular in cross-section and has a length and a width just great enough to allow the scalpel blade to slide freely through it without substantial lateral play which would permit undesirable lateral movement of the scalpel blade relative to the handle (i.e., transverse to the longitudinal axis of the handle) when the scalpel blade is in use.

Optionally, if the blade of the scalpel is replaceable, the handle can be constructed with a means for accepting disposable scalpel blades which can be replaceably secured to the blade carrier for successive use in connection with the surgical instrument of the present invention. The disposable blades can be retracted into the handle providing a scalpel which is both safe and economical to use.

FIGS. 1–5 illustrate a preferred embodiment of a surgical instrument 10 according to the present invention. As shown therein, the surgical instrument 10 comprises a hollow handle 12 having an end slot 14 and a side slot 16 formed therein. The surgical instrument 10 also includes a first sliding element such as, for example, a blade carrier 18 to which a scalpel blade 20 may be secured by any conventional means. In the embodiment of FIG. 1, the scalpel blade 20 is shown to be securable to the blade carrier 18 by means of a screw 22, but it will be apparent to those of ordinary skill in the art that any other suitable means for securing the blade 20 to the blade carrier 18, such as rivets, adhesives, or other mechanical or chemical fastening means may be used instead, if desired. In particular, the screw 22 is inserted though a hole 24 formed in the blade 20 and is threaded into a hole 26 (FIG. 5) formed in the blade carrier 18.

The blade carrier 18 is moveable between an extended in-use position (illustrated in FIG. 3), wherein the scalpel blade 20 extends out of the handle 12 through the end slot 14, and a retracted, non-use position, (illustrated in FIG. 4), wherein the scalpel blade 20 is wholly disposed within the handle 12.

The blade carrier 18 preferably moves along a longitudinal axis of the handle 12 and has a boss 28 (best shown in FIG. 1) which at least partially protrudes into the side slot 16 to the scalpel blade 20. The scalpel blade 20 is secured to the boss 28 of the blade carrier 18. The side slot 16 thus serves to guide the blade carrier 18 by confining the boss 28 to move substantially in a longitudinal path along the side slot 16 in the handle 12.

The blade carrier 18 includes at least one and preferably two fingers 30 extending from the boss 28. At least one finger 30, as shown in FIGS. 1 and 5 has a tab 32 thereon, which is engageable, when the blade carrier 18 is in the extended, in-use position (illustrated in FIG. 3) with a respective, substantially complimentary notch 34 formed in a respective adjacent edge of the side slot 16 of the handle 12. Alternatively, a tab could be provided on each of the upper and lower edges of the side slot 16, and a substantially complimentary notch could be formed in each of the fingers 30, if desired.

What is important is that each finger 30 generally have a first contoured portion (e.g., the tab 32) which is engageable with a second contoured portion (e.g., the notch 34) of the handle 12 when the blade carrier 18 is in the extended, in-use position, (shown in FIG. 3), such that each finger 30 must deflect to permit disengagement of the first contoured portion of that finger 30 from the corresponding, substantially complimentary second contoured portion of the handle 12, so that the blade carrier 18 in turn, can be moved from the extended, in-use position toward the retracted, non-use position. Thus, the first and second contoured portions need not mate perfectly with one another or be exact geometric complements to be substantially complementary.

Similarly, a third contoured portion (e.g., a notch 36), which, like the above-described second contoured portion, is substantially complimentary to the first contoured portion of a corresponding finger 30 may be provided on the upper and lower edges (as shown in FIGS. 1–5) of the side slot 16 of the handle 12 for engagement with the first contoured portions of the fingers 30 of the blade carrier 18 when the blade carrier 18 is in the retracted, non-use position, as shown in FIG. 4. The first and second or third contoured portions can be tabs and notches, interacting teeth, or bosses and recesses, or can have any other suitable contours, as desired.

When the blade carrier 18 is in the extended, in-use position, the tab 32 of each finger 30 is engaged within the corresponding, substantially complimentary notch 34 in a respective adjacent edge of the side slot 16 of the handle 12. Preferably, as shown in FIGS. 1 and 5, each finger 30 is flexible but substantially resilient such that when the blade carrier 18 is moved from the extended, in-use position of FIG. 3 toward the retracted, non-use position of FIG. 4, or vice-versa, each finger 30 will deflect toward the other finger 30, thereby disengaging the first contoured portion of the finger 30 (e.g., the tab 32) from the second contoured portion of the handle 12 (e.g., the notch 34) so that the blade carrier 18 can move from the extended, in-use position toward the retracted, non-use position.

Importantly, this disengagement does not require that the first contoured portion of the finger 30 (e.g., the tab 32) cease to contact the adjacent edge of the side slot 16 of the handle 12, but rather only that the blade carrier 18 cease to be retarded from movement by a positive locking engagement of the first contoured portion of the finger 30 with the second contoured portion of the handle 12. In fact, if the finger 30 is resilient, the tab 32 will tend to remain in contact with the adjacent edge of the side slot 16 of the handle 12. Optionally, and irrespective of the resilience of the finger(s) 30, a spring, such as a coil spring or a leaf spring, or any other suitable biasing means can be provided to bias the finger(s) 30 toward respective adjacent edge of the side slot 16. The biasing of the finger(s) 30, whether due to internal resilience of the finger(s) 30 or to a force applied to the finger(s) 30 by external means (e.g., a spring), ensures that the first contoured portion of the finger(s) 30 will automatically move to engage the corresponding second or third contoured portion of the handle 12 upon being moved substantially into alignment therewith.

The surgical instrument 10 also includes a second sliding element or a locking cam 40 that is moveable between a "locked" position and an "unlocked" position relative to the blade carrier 18. The locking cam 40 is shown in the unlocked position in FIG. 3 and is shown in the locked position in FIGS. 2, 4, and 5.

As shown in FIGS. 1 and 5, the locking cam 40 has a boss or cam 42 that extends rearwardly (as shown in FIG. 1) between the fingers 30 of the blade carrier 18 when the locking cam 40 is assembled together with the blade carrier 18 as shown in FIGS. 2–5.

As shown in FIG. 5, when the locking cam 40 is in the locked position, the cam 42 substantially inhibits deflection of the fingers 30 of the blade carrier 18 toward one another and thereby prevents disengagement of the first contoured portion 32 of each finger 30 from the corresponding second contoured portion 34 or third contoured portion 36 (depending upon whether the blade carrier 18 is in the extended, in-use position of FIG. 3 or the retracted, non-use position of FIG. 4). Further, if the finger(s) 30 do not have resilience or an external biasing means to ensure engagement, the presence of the cam 42 between the finger(s) 30 will ensure such engagement when the locking cam 40 is in the locked position. Therefore, in order to permit disengagement of the first contoured portion 32 of each finger 30 from the corresponding second or third contoured portion 34 or 36, the locking cam 40 must be moved to the unlocked position where the cam 42 permits deflection of the fingers 30 of the blade carrier 18 so that the blade carrier 18 can be moved from the extended, in-use position toward the retracted, non-use position, or vice-versa.

As illustrated in FIGS. 1 and 5, the locking cam 40 is generally constrained to move longitudinally relative to the handle 12 and the blade carrier 18 by a pair of fingers 44 which are similar to the fingers 30 of the blade carrier 18. The fingers 44 include tabs 46 which, as illustrated in phantom lines in FIG. 5, are engageable with substantially complimentary notches 48 formed in upper and lower peripheral edges (as illustrated in FIGS. 1 and 5) of the boss 28 of the blade carrier 18 when the locking cam 40 is in the locked position. The resilience of the fingers 44, together with the engagement of the tabs 46 with the substantially complimentary notches 48, prevents unintended movement of the locking cam 40 from the locked position to the unlocked position. However, because the fingers 44 of the locking cam 40 are resilient, when a user of the surgical instrument 10 manually pushes the locking cam 40 from the locked position thereof toward the unlocked position thereof, the fingers 44 deflect away from one another and permit the locking cam 40 to move toward the unlocked position so that the blade carrier 18, in turn, can move between the extended, in-use position and the retracted, non-use position, as desired by the user.

Similarly, the tabs 46 of the fingers 44 of the locking cam 40 engage respective bevels 50 (shown at the left end of the blade carrier 18 in FIG. 5) when the locking cam 40 is moved to the unlocked position. Once again, this engagement serves to prevent inadvertent movement of the locking cam 40 from the unlocked position to the locked position by a user of the surgical instrument 10, such as during surgery.

The instrument 10 can then be safely passed between members of the surgical team or the blunt end 54 of the handle 12 can be used as described above without risk of injury to the surgeon from accidental contact with the scalpel blade 20. If desired, a spring or other suitable biasing means may be provided to ensure that the locking cam 40 remains in the locked position until intentionally moved by a user of the instrument 10.

The surgical instrument 10, as shown in FIGS. 1–5, preferably has a number of other advantageous structural features, only some of which are described herein. First, textured grip surfaces are provided on the blade carrier 18 and the locking cam 40 and may also be provided on the surfaces of the handle 12 as desired above, if desired. Second, ample gripping area is provided on the handle 12 distal to the blade carrier 18, even when the blade carrier 18 is in the extended, in-use position. Third, when the blade carrier 18 is in the extended, in-use position, the scalpel blade 20 extends out of the end slot 14 of the handle 12 far enough that a user can cut using the full cutting edge of the scalpel blade 20 rather than just the point thereof. Fourth, to the extent that blood or other fluids leak into the handle 12 through the end slot 14, such fluids are permitted to drain out of the handle through the open slide slot 16 so that the blade carrier 18 and the locking cam 40 do not undesirably become jammed by a clog of dried fluids. Fifth, the handle 12 is fabricated in a two-piece construction including the handle 12 itself and an end cap 52, which may be secured to the handle 12 by a tongue-and-groove configuration, as shown, or by any other suitable means, as desired. The end cap 52 preferably has a blunt or slightly rounded end 54, which may be useful for defining surgical planes and the like. Alternatively, the handle 12 could be integrally formed in a one-piece construction, if desired.

A method of using the surgical instrument 10 described above therefore includes the steps of moving the locking cam 40 to the unlocked position if the locking cam 40 is in the locked position, moving the blade carrier 18 from the retracted, non-use position to the extended, in-use position, or vice-versa, and moving the locking cam 40 to the locked position to secure the blade carrier 18 (and thus the scalpel blade 20) in the desired extended or retracted position. It should be noted that, in the embodiment described and illustrated herein, a user moves the locking cam 40 toward the end slot (referred to by surgeons as the "distal" end of the instrument 10) to unlock the blade carrier 18 and then moves the blade carrier 18 (together with the locking cam 40) in the opposite direction (toward what surgeons refer to as the "proximal" end of the instrument 10) in order to retract the scalpel blade 20 into the handle 12. This configuration is preferable because it makes it highly unlikely that a user of the instrument 10 of the present invention will inadvertently retract the scalpel blade 20 into the handle 12 during use.

As will be appreciated by the skilled artisan, the various components of the surgical instrument 10 of the present invention can be fabricated from any desired materials, such as surgical steel or other metal, plastic, or both, for example. Preferably, regardless of what material is used, the surgical instrument 10 will have a size, weight, and feel comparable to generally available scalpels and other surgical instrument.

The foregoing description is for the purpose of teaching those skilled in the art the best mode of carrying out the invention and is to be construed as illustrative only. Numerous modifications and alternative embodiments of the invention will be apparent to those skilled in the art in view of this description, and the details of the disclosed structure may be varied substantially without departing from the spirit of the invention. Accordingly, the exclusive use of all modifications within the scope of the appended claims is reserved.

What is claimed is:

1. A surgical instrument comprising:

a hollow handle having an end slot and a side slot;

retraction means for securably moving a scalpel blade between first and second positions relative to the handle, one of which is an extended, in-use position wherein the scalpel blade extends out of the handle through the end slot, and the other of which is a retracted, non-use position wherein the scalpel blade is wholly disposed within the handle;

the retraction means including a first sliding element securable to a scalpel blade and having at least one finger extending therefrom, the finger having a first contoured portion engageable, when the retraction means is in the first position, with a second contoured portion of the handle, wherein the first and second contoured portions are substantially complementary such that the finger must deflect to permit disengagement of the first contoured portion of the finger from the second contoured portion of the handle so that the retraction means can be moved from the first position toward the second position; and locking means for locking the retraction means in one of the first and second positions;

the locking means including a second sliding element moveable between a locked position and an unlocked position and having a cam that permits deflection of the finger of the first sliding element when the second sliding element is in the unlocked position and substantially inhibits deflection of the finger of the first sliding element when the second sliding element is in the locked position.

2. The surgical instrument of claim 1, wherein the first contoured portion of the finger comprises a tab on the finger substantially projecting toward an adjacent edge of the side slot, and wherein the second contoured portion of the handle comprises a notch formed in the adjacent edge of the side slot.

3. The surgical instrument of claim 1, wherein the first contoured portion of the finger comprises a notch in an edge of the finger adjacent an edge of the side slot, and wherein the second contoured portion of the handle comprises a tab on the adjacent edge of the side slot substantially projecting toward the finger.

4. The surgical instrument of claim 1, wherein the sliding element has a pair of fingers, each having a contoured portion that, when the retraction means is in the first position, is engageable with a respective contoured portion of the handle, wherein the contoured portion of each finger is substantially complementary to the respective contoured portion of the handle such that each finger must deflect to permit disengagement of the contoured portion of that finger from the respective contoured portion of the handle so that the retraction means can be moved from the first position toward the second position.

5. The surgical instrument of claim 4, wherein the cam of the second sliding element permits deflection of both fingers when the second sliding element is in the unlocked position and substantially inhibits deflection of both fingers when the second sliding element is in the locked position.

6. The surgical instrument of claim 1, wherein the handle has a third contoured portion with which the first contoured portion of the finger is engageable when the retraction means is in the second position, and wherein the first and third contoured portions are substantially complementary such that the finger must deflect to permit disengagement of the first contoured portion from the third contoured portion so that the retraction means can be moved from the second position toward the first position.

7. The surgical instrument of claim 6, wherein the first contoured portion of the finger is one of a tab and a notch, and each of the second and third contoured portions of the handle is the other of a tab and a notch.

8. The surgical instrument of claim 1, further including means for biasing the finger toward an adjacent edge of the side slot.

9. The surgical instrument of claim 1, wherein the finger is flexible but substantially resilient.

10. A surgical instrument comprising:
   a hollow handle having an end slot and a side slot; and
   a blade carrier securable to a scalpel blade and moveable between first and second positions relative to the handle, one of said first and second positions being an extended, in-use position wherein the scalpel blade extends out of the handle through the end slot, and the other of said first and second positions being a retracted, non-use position wherein the scalpel blade is wholly disposed within the handle;
   the blade carrier having at least one finger extending therefrom, the finger having a first contoured portion engageable, when the blade carrier is in the first position, with a second contoured portion of the handle, wherein the first and second contoured portions are substantially complementary such that the finger must deflect to permit disengagement of the first contoured portion of the finger from the second contoured portion of the handle so that the blade carrier can be moved from the first position toward the second position; and
   a locking cam moveable between a locked position wherein the locking cam substantially inhibits deflection of the finger of the blade carrier and an unlocked position wherein the locking cam permits deflection of the finger of the blade carrier.

11. The surgical instrument of claim 10, wherein the first contoured portion of the finger comprises a tab on the finger substantially projecting toward an adjacent edge of the side slot, and wherein the second contoured portion of the handle comprises a notch formed in the adjacent edge of the side slot.

12. The surgical instrument of claim 10, wherein the first contoured portion of the finger comprises a notch in an edge of the finger adjacent an edge of the side slot, and wherein the second contoured portion of the handle comprises a tab on the adjacent edge of the side slot substantially projecting toward the finger.

13. The surgical instrument of claim 10, wherein the blade carrier has a pair of fingers, each having a contoured portion that, when the blade carrier is in the first position, is engageable with a respective contoured portion of the handle, wherein the contoured portion of each finger is substantially complementary to the respective contoured portion of the handle such that each finger must deflect to permit disengagement of the contoured portion of that finger from the respective contoured portion of the handle so that the blade carrier can be moved from the first position toward the second position.

14. The surgical instrument of claim 13, wherein the cam of the second sliding element permits deflection of both fingers when the second sliding element is in the unlocked position and substantially inhibits deflection of both fingers when the second sliding element is in the locked position.

15. The surgical instrument of claim 10, wherein the handle has a third contoured portion with which the first contoured portion of the finger is engageable when the blade carrier is in the second position, and wherein the first and third contoured portions are substantially complementary such that the finger must deflect to permit disengagement of the first contoured portion from the third contoured portion so that the blade carrier can be moved from the second position toward the first position.

16. The surgical instrument of claim 15, wherein the first contoured portion of the finger is one of a tab and a notch, and each of the second and third contoured portions of the handle is the other of a tab and a notch.

17. The surgical instrument of claim 10, further including means for biasing the finger toward an adjacent edge of the side slots.

18. The surgical instrument of claim 10, wherein the finger is flexible but substantially resilient.

19. A method of locking a scalpel blade of a surgical instrument having a hollow handle with an end slot and a slide slot, a retraction means for securably moving a scalpel blade between first and second positions, one of which is an extended, in-use position wherein the scalpel blade extends out of the handle through the end slot, and the other of which is a retracted, non-use position wherein the scalpel blade is wholly disposed within the handle, said retraction means including a first sliding element securable to a scalpel blade and having at least one finger extending therefrom, the finger having a first contoured portion engageable, when the retraction means is in the first position, with a second contoured portion of the handle, wherein the first and second contoured portions are substantially complementary such that the finger must deflect to permit disengagement of the first contoured portion of the finger from the second contoured portion of the handle so that the retraction means can be moved from the first position toward the second position, and a locking means including a second sliding element moveable between a locked position and an unlocked position and having a cam that permits deflection of the finger of the first sliding element when the second sliding element is in the unlocked position and substantially inhibits deflection of the finger of the first sliding element when the second sliding element is in the locked position, the method comprising the steps of:
   moving the retraction means to one of the first and second positions relative to the handle; and
   locking the retraction means in one of the first and second positions with the locking means.

20. A method of using a retractable surgical scalpel including a hollow handle having an end slot and a side slot, a blade carrier securable to a scalpel blade and moveable between first and second positions relative to the handle and having a finger having a first contoured portion engageable with a substantially complementary second contoured portion of the handle when the blade carrier is in the first position and with a substantially complementary third contoured portion of the handle when the blade carrier is in the second position, and a locking cam moveable between a locked position wherein deflection of the finger is substantially inhibited and an unlocked position wherein deflection of the finger is permitted, the method comprising the steps of:

moving the locking cam to the unlocked position if the locking cam is in the locked position;

moving the blade carrier from one of the first and second positions to the other of the first and second positions; and moving the locking cam to the locked position.

* * * * *